(12) United States Patent
Mayer

(10) Patent No.: US 6,183,448 B1
(45) Date of Patent: *Feb. 6, 2001

(54) NEEDLELESS INJECTION SITE

(76) Inventor: Bruno Franz P. Mayer, 9732 Willow Glenn Cir., Santa Ana, CA (US) 92705

( * ) Notice: Under 35 U.S.C. 154(b), the term of this patent shall be extended for 0 days.

This patent is subject to a terminal disclaimer.

(21) Appl. No.: 08/966,337

(22) Filed: Nov. 7, 1997

Related U.S. Application Data

(63) Continuation-in-part of application No. 08/735,217, filed on Oct. 22, 1996, now Pat. No. 5,836,923, which is a continuation-in-part of application No. 08/699,848, filed on Aug. 20, 1996, now Pat. No. 5,820,601, which is a continuation-in-part of application No. 08/493,744, filed on Jun. 22, 1995, now Pat. No. 5,616,130, which is a continuation-in-part of application No. 08/401,854, filed on Mar. 10, 1995, now Pat. No. 5,616,129, which is a continuation-in-part of application No. 08/262,994, filed on Jun. 20, 1994, now Pat. No. 5,470,319.

(51) Int. Cl.⁷ ............................ A61M 5/00; A61M 5/178

(52) U.S. Cl. ............................................ 604/256; 604/167

(58) Field of Search ..................... 604/256, 246, 604/93, 164, 167, 257, 905, 129; 251/149.1, 149.8

(56) References Cited

U.S. PATENT DOCUMENTS

| | | | |
|---|---|---|---|
| 3,977,555 | 8/1976 | Larson | 215/247 |
| 4,063,460 | 12/1977 | Svensson | 73/425.6 |
| 4,134,512 | 1/1979 | Nugent | 215/247 |
| 4,246,899 | 1/1981 | Loseff | 128/276 |
| 4,301,936 | 11/1981 | Percarpio | 215/247 |

(List continued on next page.)

FOREIGN PATENT DOCUMENTS

| | | |
|---|---|---|
| 3105437 | 10/1982 | (DE) . |
| 3105437 | 6/1986 | (DE) . |
| 0309771 | 3/1928 | (EP) . |
| 0 309 771 | 5/1989 | (EP) . |
| 0544581 | 11/1992 | (EP) . |
| WO 93/05838 | 1/1993 | (WO) . |
| WO 93/05839 | 1/1993 | (WO) . |
| WO 9305838 | 4/1993 | (WO) . |
| WO 9305839 | 4/1993 | (WO) . |
| WO 9311828 | 6/1993 | (WO) . |
| WO 600107 | 1/1996 | (WO) . |
| WO 97/21464 | 6/1997 | (WO) . |
| WO 9721464 | 6/1997 | (WO) . |

OTHER PUBLICATIONS

Safe Tech Medical Products, Inc., "Stat–Link", "Universal Connector With Valve", 2 pages ( no publication date).

\* cited by examiner

*Primary Examiner*—Sharon Kennedy
*Assistant Examiner*—Michael J Hayes
(74) *Attorney, Agent, or Firm*—Stetina Brunda; Garred & Brucker

(57) ABSTRACT

A needleless injection site comprising a housing which defines a fluid passage. Disposed within the housing is a reseal member which includes an openable and closable aperture, and an expandable and collapsible reservoir. The reseal member normally resides in a first position within the housing wherein the aperture is closed and the reservoir is collapsed. The reseal member is deformable such that the application of compressive pressure thereto will facilitate the movement thereof within the housing to a second position wherein the reservoir is expanded and the aperture is opened and placed into communication with the fluid passage and the reservoir. The removal of the compressive pressure from the reseal member will facilitate the resilient return thereof to the first position wherein the aperture is closed and the reservoir is collapsed. The collapse of the reservoir is adapted to prevent the creation of a vacuum within the fluid passage when the reseal member resiliently returns to the first position.

35 Claims, 5 Drawing Sheets

U.S. PATENT DOCUMENTS

| | | | |
|---|---|---|---|
| 4,338,764 | 7/1982 | Percarpio | 53/432 |
| 4,838,855 | 6/1989 | Lynn | 604/49 |
| 4,874,377 | 10/1989 | Newgard et al. | 604/167 |
| 5,064,416 | 11/1991 | Newgard et al. | 604/167 |
| 5,100,394 | 3/1992 | Dudar et al. | 604/283 |
| 5,122,123 | 6/1992 | Vaillancourt | 604/192 |
| 5,122,129 | 6/1992 | Olson et al. | 604/905 |
| 5,135,489 | 8/1992 | Jepson et al. | 604/48 |
| 5,154,703 | 10/1992 | Bonaldo | 604/244 |
| 5,158,554 | 10/1992 | Jepson et al. | 604/283 |
| 5,171,234 | 12/1992 | Jepson et al. | 604/283 |
| 5,188,620 | 2/1993 | Jepson et al. | 604/283 |
| 5,203,775 | 4/1993 | Frank et al. | 604/256 |
| 5,234,413 | 8/1993 | Wonder et al. | 604/248 |
| 5,273,533 | 12/1993 | Bonaldo | 604/83 |
| 5,286,453 | 2/1994 | Pope | 422/400 |
| 5,324,256 | 6/1994 | Lynn | 604/49 |
| 5,360,012 | 11/1994 | Ebara et al. | 128/764 |
| 5,360,413 * | 11/1994 | Leason et al. | 604/249 |
| 5,380,306 | 1/1995 | Brinon | 604/244 |
| 5,470,319 | 11/1995 | Mayer | 604/167 |
| 5,474,544 | 12/1995 | Lynn | 604/283 |
| 5,487,728 | 1/1996 | Vaillancourt | 604/86 |
| 5,509,912 | 4/1996 | Vaillancourt et al. | 604/283 |
| 5,514,116 | 5/1996 | Vaillancourt . | |
| 5,514,118 | 5/1996 | Vaillancourt et al. | 604/283 |
| 5,520,666 | 5/1996 | Choudhury et al. | 604/283 |
| 5,549,566 | 8/1996 | Elias et al. | 604/167 |
| 5,549,577 * | 8/1996 | Siegel et al. | 604/256 |
| 5,569,235 * | 10/1996 | Ross et al. | 604/403 |
| 5,669,891 | 9/1997 | Vaillancourt | 604/283 |
| 5,676,346 | 10/1997 | Leinalng | 251/149.1 |
| 5,685,866 | 11/1997 | Lopez | 604/249 |
| 5,688,254 | 11/1997 | Lopez et al. | 604/283 |
| 5,690,612 | 11/1997 | Lopez et al. | 604/93 |
| 5,694,686 | 12/1997 | Lopez | 29/890.132 |
| 5,695,466 | 12/1997 | Lopez et al. | 604/93 |
| 5,699,821 | 12/1997 | Paradis | 137/1 |
| 5,700,248 | 12/1997 | Lopez | 604/249 |
| 5,738,663 | 4/1998 | Lopez | 604/249 |
| 5,807,348 * | 9/1998 | Zinger et al. | 604/246 |

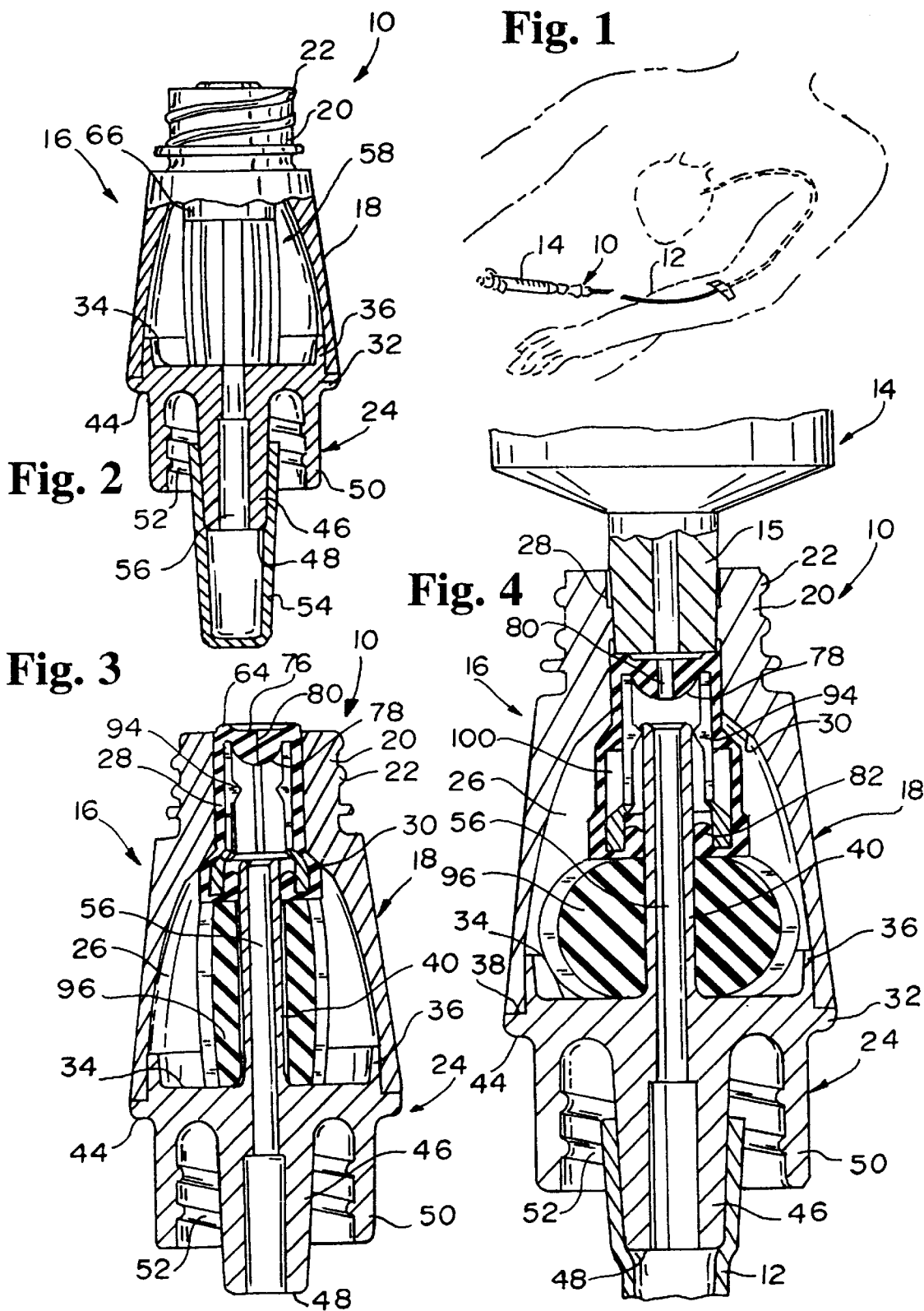

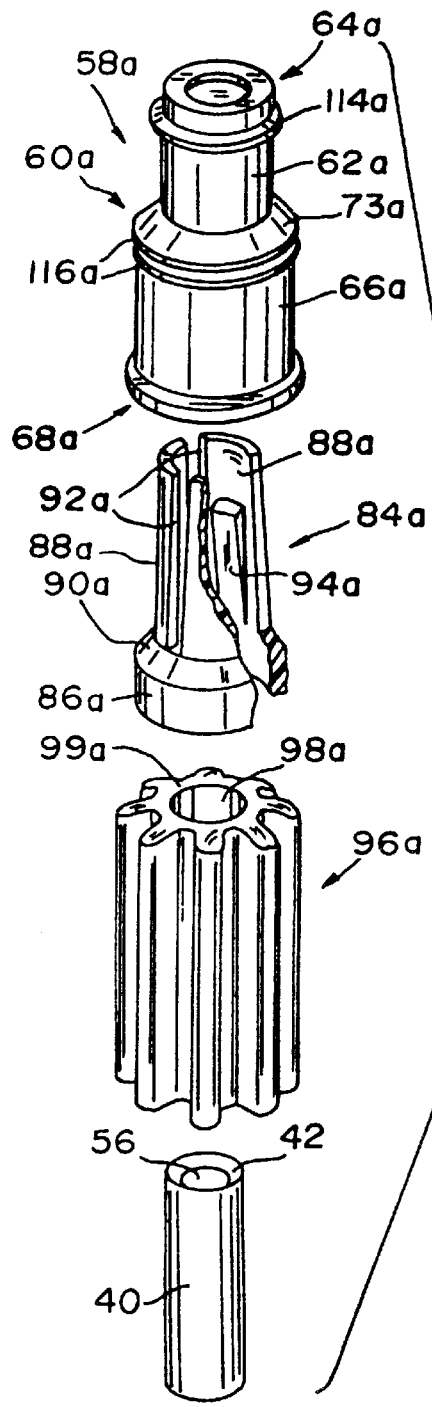
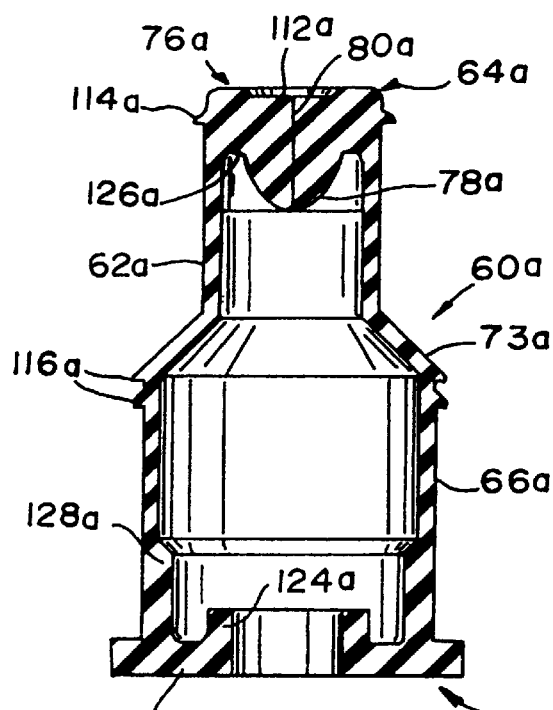
Fig. 7a
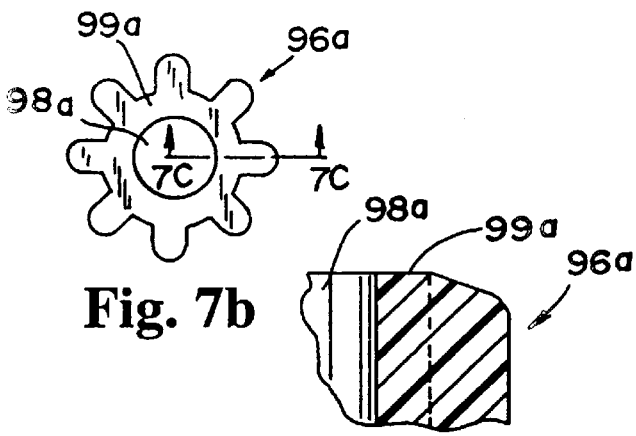
Fig. 7b
Fig. 7c
Fig. 7

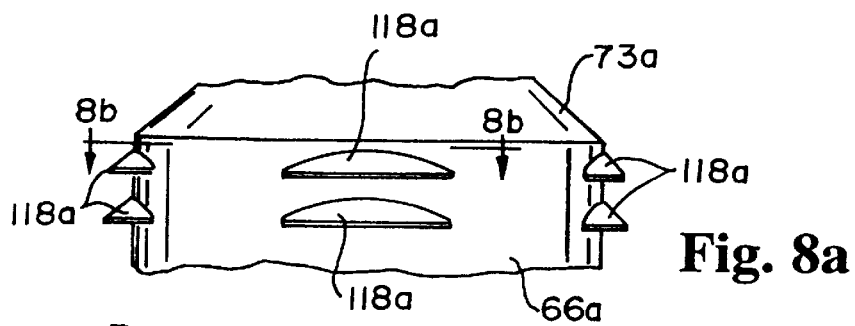
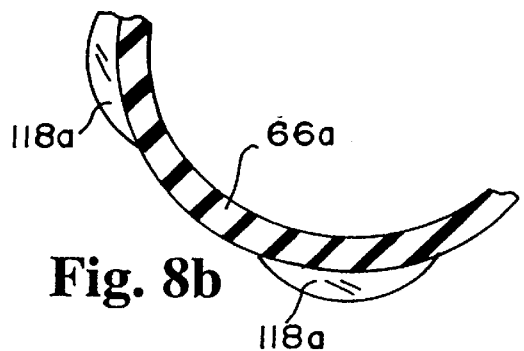
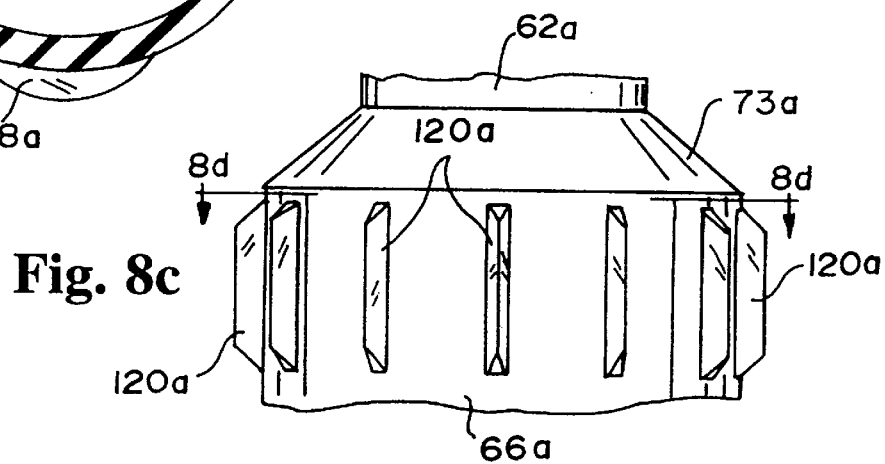
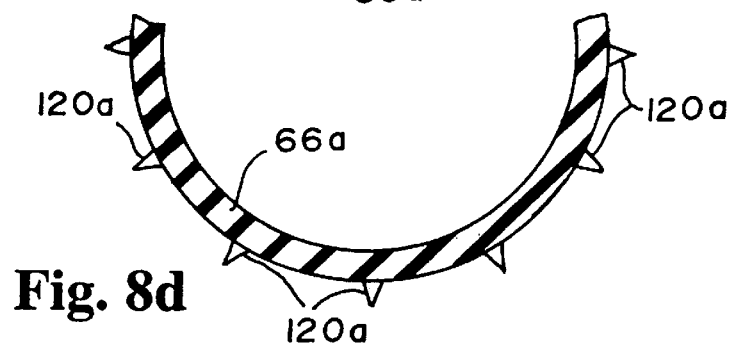

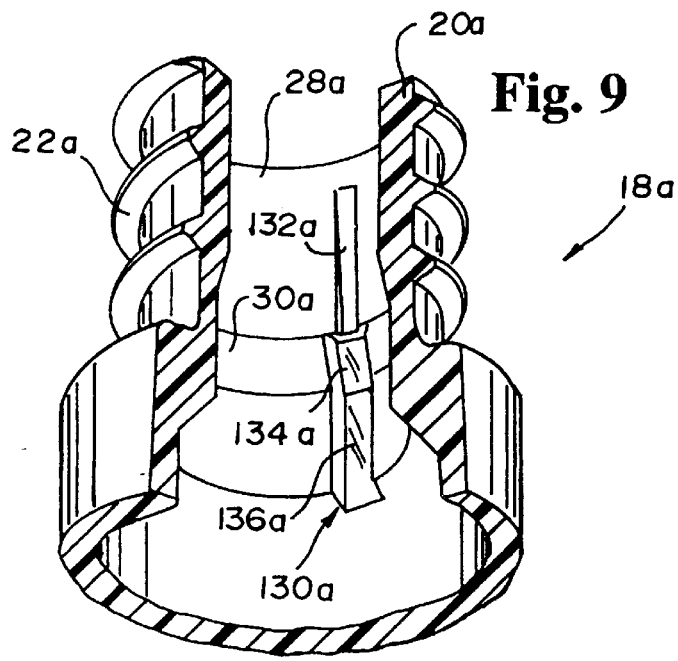
Fig. 9
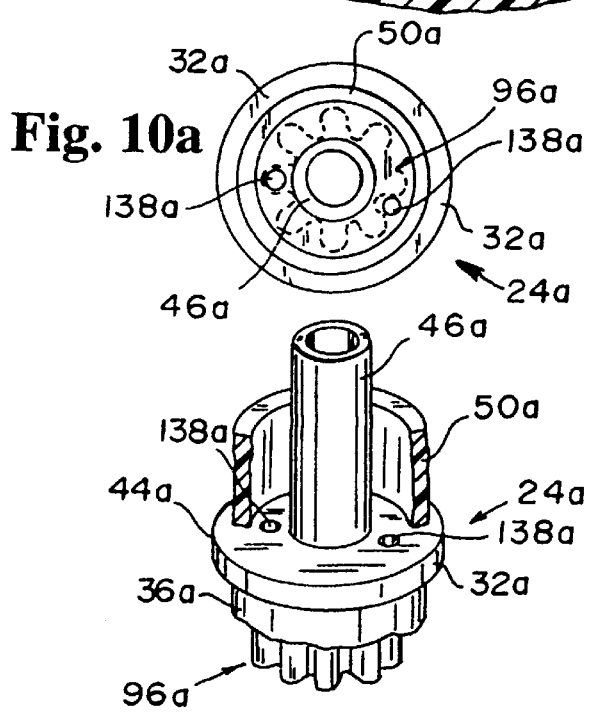
Fig. 10a
Fig. 10
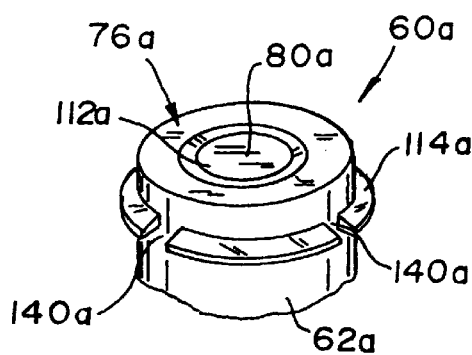
Fig. 11

NEEDLELESS INJECTION SITE

RELATED APPLICATIONS

The present application is a continuation-in-part of U.S. application Ser. No. 08/735,217, U.S. Pat. No. 5,836,923 entitled NEEDLESS INJECTION SITE WITH FIXED FLOW RATE filed Oct. 21, 1996, which is a continuation-in-part of U.S. application Ser. No. 08/699,848, U.S. Pat. No. 5,820,601 entitled NEEDLELESS INJECTION SITE filed Aug. 20, 1996, which is a continuation-in-part of U.S. patent application Ser. No. 08,493,744 filed Jun. 22, 1995 now U.S. Pat. No. 5,616,130 entitled NEEDLELESS INJECTION SITE issued Apr. 1, 1997, which is a continuation-in-part of U.S. patent application Ser. No. 08,401,854 filed Mar. 10, 1995 now U.S. Pat. No. 5,616,129 entitle NEEDLELESS INJECTION SITE issued Apr. 1, 1997, which is a CIP of U.S. application Ser. No. 08,252,994 filed May 10, 1994 now U.S. Pat. No. 5,470,319, the disclosures of which are expressly incorporated herein by reference.

FIELD OF THE INVENTION

The present invention relates generally to the medical arts, and more particularly to a needleless injection site for use in intravenous infusion applications.

BACKGROUND OF THE INVENTION

It is common medical practice to intravenously infuse various fluids or medicaments into a blood vessel of a patient (e.g., a vein or artery). Such infusion is typically accomplished by the insertion of a hollow introducer needle into a target blood vessel. The introducer needle is fluidly connected to one end of an elongate, flexible tube or fluid line, the opposite end of which is fluidly connected to a solution bag. The solution bag itself is typically suspended above the patient so as to allow gravity to facilitate the flow of fluid downwardly through the fluid line and into the patient's blood vessel via the introducer needle which remains operatively positioned therewithin. The fluid tube and solution bag are connected to each other via a metering apparatus which controls the infusion rate of fluid from the bag into the tube.

In many intravenous infusion assemblies, an injection site is fluidly coupled within the tubing intermediate the introducer needle and the solution bag. The injection site typically has a Y-shaped configuration and comprises a tubular main body portion having a tubular side arm portion in fluid communication therewith. The distal end of the side arm portion is fluidly connected to the solution bag via an upper segment of the tubing, with the bottom end of the main body portion being fluidly connected to the introducer needle via a lower segment of the tubing. The top end of the main body portion is itself covered by a diaphragm which is typically fabricated from rubber or a similar resilient material.

The inclusion of the injection site within the tubing allows various medications to be selectively infused into the blood vessel of the patient by the addition thereof to the solution flowing from the solution bag into the blood vessel via the upper tubing segment, injection site, lower tubing segment and introducer needle. This supplemental infusion is typically accomplished through the utilization of a conventional syringe, the needle of which pierces and is extended through the diaphragm disposed on the top end of the main body portion of the injection site. Subsequent to the expulsion of the medication from within the syringe and into the flowing solution, the needle is retracted out of the main body portion of the injection site, with the aperture created in the diaphragm due to the passage of the needle therethrough being substantially closed upon such retraction due to the resiliency of the diaphragm. As will be recognized, the incorporation of the injection site within the tubing allows various medications to be intravenously administered to the patient through the existing infusion site within the blood vessel, thus eliminating the need to subject the patient to additional needle sticks.

Though providing certain benefits to the patient, the injection sites constructed in accordance with the prior art possess certain deficiencies which detract from their overall utility. As previously explained, the use of such injection sites typically requires that the needle of the conventional syringe be extended through (i.e., puncture) the diaphragm attached to the top end of the main body portion of the injection site. However, the necessity of having to utilize a syringe with a needle to facilitate the introduction of the medication into the solution flow is undesirable due to the risk of inadvertent needle sticks.

In recognition of this deficiency, there has also been developed in the prior art needleless injection sites which incorporate a diaphragm adapted to assume open and closed configurations without having a needle inserted thereinto. Though these needleless injection sites eliminate the necessity of having to puncture the diaphragm with a needle, they also possess certain deficiencies which detract from their overall utility. Foremost of these deficiencies is the difficulty associated with disinfecting the injection site, and in particular the diaphragm thereof, subsequent to medication being infused thereinto. In this respect, after each use of the injection site the diaphragm must be cleaned, with such cleaning typically being accomplished through the application of alcohol or a similar disinfecting agent thereto. However, due to the configuration of the diaphragm, complete and effective disinfection thereof is often difficult to achieve, thus increasing the risk of the inadvertent introduction of contaminates into the solution stream upon subsequent uses of the injection site.

In an effort to overcome the deficiencies associated with the prior art injection sites, Applicant developed the needleless injection sites disclosed in the previously identified issued patents and co-pending applications which are the parent cases of the present application. The present needleless injection site constitutes an improvement over those disclosed in the parent cases. In this respect, the present injection site is provided with design features which are adapted to prevent the inadvertant obstruction of the fluid flow path, and to increase the level of positive flow within the fluid flow path such that the withdrawal of a needled or non-needled introducer from within the injection site does not cause a vacuum to be pulled within a tubular fluid line connected thereto.

SUMMARY OF THE INVENTION

In accordance with the present invention, there is provided a needleless injection site which comprises a housing. The housing itself comprises an interior chamber, a central opening which communicates with the interior chamber, and an elongate, proximally extending dilator projection portion which defines a fluid passage and extends toward the central opening in coaxial alignment therewith.

In addition to the housing, the present needleless injection site comprises a reseal member which is disposed within the central opening and the interior chamber of the housing. The reseal member includes an elastically openable and closable aperture, and an expandable and collapsible reservoir which, when expanded, is adapted to retain a volume of fluid. The reseal member normally resides in a first position within the housing wherein the aperture is closed and the reservoir is collapsed. The reseal member is selectively deformable such that the application of distally directed compressive pressure thereto will cause the same to distally advance within the housing to a second position wherein the reservoir is expanded and the aperture is opened and placed into communication with the fluid passage and the reservoir. The removal of the distally directed compressive pressure from the reseal member facilitates the resilient return thereof to the first position wherein the aperture is closed and the reservoir is collapsed. The collapse of the reservoir which occurs when the reseal member resiliently returns to its first position forces the fluid within the reservoir into the fluid passage which effectively prevents the creation of a vacuum therewithin.

In accordance with the present invention, the reseal member comprises a resilient body having a distal end and a proximal end which defines inner and outer surfaces. Extending through the proximal end between the inner and outer surfaces thereof is the elastically openable and closable aperture. The proximal end of the body is defined by a generally cylindrical proximal portion thereof, with the distal end being defined by a generally cylindrical distal portion of the body. The proximal and distal portions are separated by a beveled shoulder formed therebetween, and are sized such that the diameter of the distal portion exceeds the diameter of the proximal portion.

In the present injection site, the inner surface of the proximal end of the body has a generally semi-spherical configuration to prevent any inadvertant tearing of the proximal end when the reseal member is moved between its first and second positions. Additionally, preferably formed in the outer surface of the proximal end of the body is a circularly configured depression which is centrally positioned within the outer surface. The aperture of the reseal member extends axially between the approximate center of the circular depression formed within the outer surface and the apex of the semi-spherical inner surface. The formation of the depression within the outer surface causes distally directed compressive pressure exerted against the proximal end by the tip of a syringe or other fluid injecting device to be applied to the periphery of the outer surface about the aperture. Such peripheral application of compressive pressure eliminates axial bulge of the proximal end of the body during the movement of the reseal member from its first position to its second position. Such axial bulge, if not prevented, could obstruct flow through the aperture of the reseal member.

Formed on the proximal portion of the reseal member body is a centering ring which extends thereabout and has a generally wedge-shaped cross-sectional configuration. The centering ring is used to maintain the aperture in coaxial alignment with the fluid passage defined by the dilator projection portion as the reseal members move between its first and second positions. Maintaining such coaxial alignment ensures that the aperture will elastically expand to its open position when the reseal member is distally advanced within the housing. The centering ring may optionally include one or more notches disposed therein for venting the interior chamber of the housing during the movement of the reseal members from its first position to its section position.

In addition to the formation of the centering ring upon the proximal portion of the body, preferably formed on the distal portion of the body adjacent the beveled shoulder thereof is at least one, and preferably a pair of compression rings which extend thereabout. Like the centering ring, each of the compression rings preferably has a generally wedge-shaped cross-sectional configuration. The compression rings effectively increase the diameter of the distal portion of the reseal member body for purposes of assisting in the collapse of the reservoir when the reseal member moves from its second position to its first position.

As an alternative to the compression rings, the distal portion of the body may include at least one, and preferably two sets of arcuately contoured compression tabs which are formed thereon and extend thereabout adjacent the beveled shoulder of the body. Each set preferably comprises four (4) compression tabs which are separated by intervals of approximately 90 degrees. The compression tabs of each set are preferably in longitudinal alignment with respective ones of the compression tabs of the other set. As a further alternative to the compression rings, the distal portion of the body may include a plurality of elongate, longitudinally extending compression ribs formed thereon adjacent the beveled shoulder of the body. The compression ribs each preferably have a generally wedge-shaped cross-sectional configuration, and extend about the distal portion of the body in equidistantly spaced relation to each other.

In addition to either the compression rings, compression tabs, or compression ribs, formed on the distal portion of the reseal member body is an annular flange which extends about and radially inward from the distal end of the body. This flange is used to form a seal against the dilator projection portion when the reseal member is inserted into the interior of the housing. The seal formed by the flange of the body is maintained during the movement of the body along the dilator projection portion as the reseal member is moved between its first and second positions.

The reseal member further comprises a radial leaf spring which is disposed within the body. The radial leaf spring comprises a base portion and a plurality of flexible leaf portions which extend from the base portion and include slots therebetween. The leaf portions are adapted to apply a radially inward biasing force to the proximal end of the body which normally closes the aperture when no distally directed compressive pressure is applied to the outer surface of the proximal end. The reservoir of the reseal member is defined between the radial leaf spring and the body, with the slots defining fluid flow channels between the aperture and the reservoir when the reseal member is moved to its second position, and between the reservoir and the fluid passage during the return of the reseal member to its first position. In the present needleless injection site, the volumetric capacity of the reservoir when expanded is preferably not less than the product of the internal diameter of the fluid passage and the travel distance of the reseal member when moved between its first and second positions. More particularly, the volumetric capacity of the expanded reservoir is preferably about 0.035 ml.

In addition to the body and the radial leaf spring, the reseal member comprises an elongate, generally cylindrical doughnut spring having a chamfered first end, a portion of which is abutted against the distal end of the body, and a second end which is abutted against the housing. Extending longitudinally or axially through the doughnut spring is a bore which is sized and configured to accommodate the dilator projection portion of the housing. The doughnut spring preferably includes a splined or fluted outer surface which defines a plurality of elongate channels extending longitudinally therewithin. The splined configuration of the doughnut spring reduces the level of friction exerted by it against the dilator projection portion as the reseal member is moved between its first and second positions, and also facilitates faster and easier insertion of the dilator projection portion into the bore during the assembly of the present injection site. The doughnut spring is preferably sized such that a slight compression force (i.e., a pre-load) is applied thereto when the reseal member is in its first position. Both the body and the doughnut spring of the reseal member are preferably fabricated from silicone or similar materials.

The dilator projection portion of the housing extends into the reseal member, and more particularly is extended through the bore of the doughnut spring and into the radial leaf spring. As previously indicated, the annular flange formed about and extending radially inward from the distal end of the reseal member body is abutted against the dilator projection portion when the same is extended through the bore into the reseal member, thus creating the fluid-tight seal therebetween. The application of distally directed pressure to the outer surface of the proximal end of the body causes the radial leaf spring to be distally advanced over the dilator projection portion. The resultant outward flexion of the leaf portions facilitates the opening of the aperture via the radial expansion thereof. Such outward flexion of the leaf portions of the radial leaf spring is assisted by downwardly sloping ramp portions which are formed on the inner surfaces of respective ones of the leaf portions and extend to the base portion of the radial leaf spring. These ramp portions engage the dilator projection portion when the reseal member is distally advanced thereover, thus resulting in the outward flexion of the leaf portions and the opening of the aperture. The sizing of the ramp portions is adapted to prevent the bowing of the leaf portions as they are flexed outwardly by the distal advancement of the reseal member over the dilator projection portion. The movement of the reseal member toward its second position facilitates the expansion of the reservoir from its normally collapsed state.

The removal of the distally directed compressive pressure from the outer surface of the proximal end of the body causes the radial leaf spring to be proximally withdrawn from over the dilator projection portion. Such proximal movement facilitates the resilient closure of the aperture, and the compression or collapse of the reservoir by the housing. When the reseal member is moved to its second position, the doughnut spring is compressed between the distal end of the reseal member body and the housing, with such compression typically causing the splines of the outer surface of the doughnut spring to assume a generally serpentine configuration. The movement of the reseal member back to its first position is facilitated by the resilient return of the doughnut spring to its normal, pre-loaded configuration.

When the reseal member is distally advanced to its second position, intravenous fluid introduced thereinto via the open aperture flows into the expanded reservoir via the slots defined between the leaf portions of the radial leaf spring. In addition to flowing into the reservoir, such fluid flows directly into the fluid passage defined by the dilator projection portion of the housing. When the reseal member resiliently returns to its first position, the resultant collapse of the reservoir by the housing forces the fluid from therewithin back through the slots defined between the leaf portions and into the fluid passage, thus creating a zero or positive displacement therewithin, i.e., preventing a vacuum from being created within the fluid passage. As previously indicated, the reservoir is preferably sized to displace approximately 0.035 ml of retained fluid volume, with the volumetric capacity of the reservoir preferably being equal to or greater than the inner diameter of the fluid passage multiplied by the axial travel distance of the reseal member when the same moves from its first position to its second position.

The housing of the present needleless injection site comprises an upper section which defines the central opening, and a lower section which is attached to the upper section. When attached to each other, the upper and lower sections collectively define the interior chamber. The lower section itself preferably comprises a central portion which is attached to the upper section via a sonic weld, and includes the dilator projection portion extending proximally from one side thereof and an adaptor portion extending distally from the opposite side thereof. The adaptor portion of the lower section preferably comprises a tubing connection having a tapered outer surface and a blunt distal tip. Slidably extensible over and frictionally maintainable upon the tubing connection is a breather cap. The lower section further includes a distal lock region which circumvents the adaptor portion and preferably includes a plurality of Luer thread formed therewithin. The upper section of the housing may optionally include one or more elongate slots which are disposed within and extend along portions of the inner surface of the upper section which define the central opening and partially define the interior chamber. The slot(s) are used for venting the interior chamber during the movement of the reseal member from its first position to its second position. Alternatively, the lower section of the housing may optionally include two or more apertures disposed therein which are also used for venting the interior chamber during the movement of the reseal member from its first position to its second position.

BRIEF DESCRIPTION OF THE DRAWINGS

These, as well as other features of the present invention, will become more apparent upon reference to the drawings wherein:

FIG. 1 is a perspective view illustrating an exemplary manner in which the needleless injection site constructed in accordance with the present invention is used to facilitate fluid infusion into an anatomical passage;

FIG. 2 is a partial cross-sectional view of the needleless injection site constructed in accordance with the present invention;

FIG. 3 is a cross-sectional view of the needleless injection site shown in FIG. 2, illustrating the reseal member thereof in a first, closed position;

FIG. 4 is a cross-sectional view of the needleless injection site shown in FIG. 2, illustrating the reseal member thereof as deformed into a second, open position;

FIG. 7 is an exploded view illustrating an alternative embodiment of the reseal member;

FIG. 7a is a cross-sectional view of the body component of the reseal member shown in FIG. 7;

FIG. 7b is a top plan view of the doughnut spring component of the reseal member shown in FIG. 7;

FIG. 7c is a partial cross-sectional view of the doughnut spring component of the reseal member taken along line 7c—7c of FIG. 7b;

FIG. 8a is a partial side-elevational view of a first alternative embodiment of the body component of the reseal member shown in FIG. 7a;

FIG. 8b is a cross-sectional view taken along line 8b—8b of FIG. 8a;

FIG. 8c is a partial side-elevational view of a second alternative embodiment of the body component of the reseal member shown in FIG. 7a;

FIG. 8d is a cross-sectional view taken along line 8d—8d of FIG. 8c;

FIG. 9 is a cut-away perspective view of an alternative embodiment of the upper section of the needleless injection site housing;

FIG. 10 is a cut-away partial perspective view of an alternative embodiment of the lower section of the needleless injection site housing;

FIG. 10a is a bottom plan view of the lower section of the needleless injection site housing shown in FIG. 10; and FIG. 11 is a partial perspective view of an alternative embodiment of the reseal member body shown in FIGS. 7 and 7a.

DETAILED DESCRIPTION OF THE PREFERRED EMBODIMENTS

Figure 5:
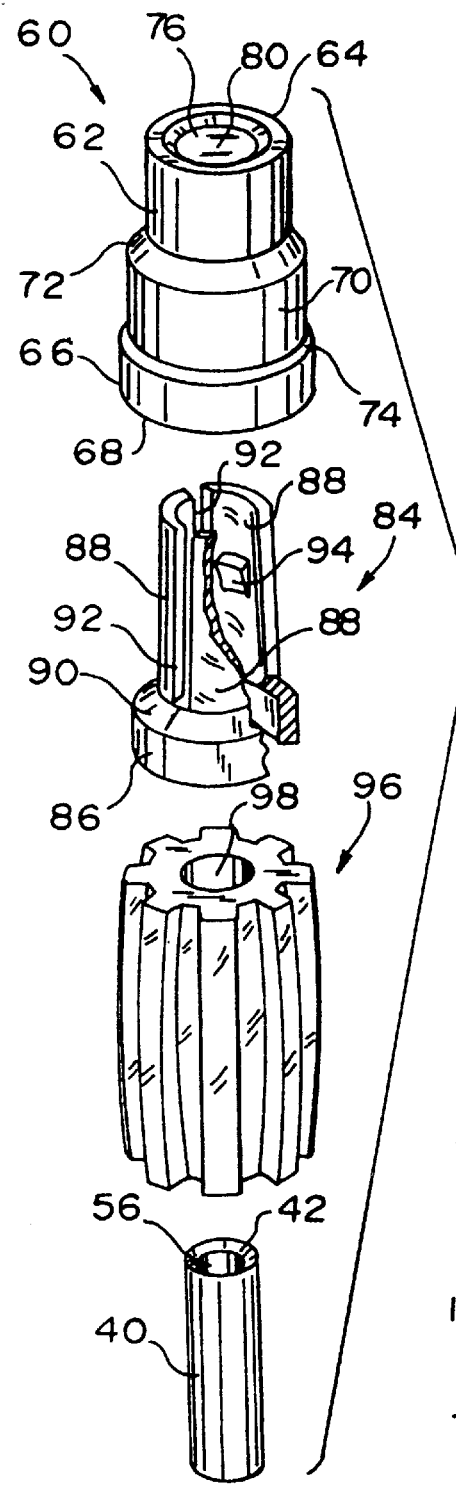
FIG. 5 is an exploded view illustrating the components comprising the reseal member shown in FIGS. 3 and 4.

Referring now to the drawings wherein the showings are for purposes of illustrating preferred embodiments of the present invention only, and not for purposes of limiting the same, FIG. 1 illustrates a needleless injection site 10 constructed in accordance with a first embodiment of the present invention as used to facilitate the infusion of a medicament into a blood vessel (e.g., a vein or artery) of a patient. As will be discussed in more detail below, the needleless injection site 10 of the present invention presents advantages over those constructed in accordance with the prior art in that the same is specifically adapted to create a zero or positive displacement of fluid within the fluid line 12 extending from the injection site 10 to the blood vessel of the patient when a non-needled introducer 14 is withdrawn from therewithin. Importantly, such zero or positive displacement of fluid prevents a vacuum from being created within the fluid line 12, thus eliminating any back-flow of blood thereinto. As will be recognized, any back-flow of blood into the fluid line 12 is highly undesirable, in that the coagulation thereof may obstruct the fluid line 12 or create a clot which inadvertently passes into the blood vessel of the patient.

Referring now to FIGS. 2–5, the injection site 10 of the present invention comprises a hollow housing 16. The housing 16 itself comprises an upper section 18 which defines a reduced diameter proximal portion 20 having Luer threads 22 formed on the outer surface thereof. In addition to the upper section 18, the housing 16 includes a lower section 24 which is rigidly attached to the upper section 18. When attached to each other, the upper and lower sections 18, 24 collectively define an interior chamber 26. In this respect, the proximal portion 20 of the upper section 18 defines a central opening 28 which communicates with the interior chamber 26. As best seen in FIGS. 3 and 4, the transition between the central opening 28 and interior chamber 26 is defined by an annular, inclined shoulder 30 formed within the inner surface of the upper section 18.

The lower section 24 of the housing 16 includes a central portion 32 defining a generally planar, circularly configured proximal surface 34 which is circumvented by an annular flange portion 36. Formed within the outer surface of the central portion 32 and extending thereabout is a continuous, annular shoulder 38. When the upper and lower sections 18, 24 are attached to each other, the distal rim of the upper section 18 is abutted against the shoulder 38, with the flange portion 36 extending along the inner surface of the upper section 18 in direct contact therewith. The attachment of the upper and lower sections 18, 24 to each other is preferably facilitated by a sonic weld between the distal rim of the upper section 18 and the shoulder 38 defined by the lower section 24. However, it will be recognized by those of ordinary skill in the art that alternative attachment methods, such as the use of adhesives, may be employed in the injection site 10. The upper and lower sections 18, 24 are sized such that when rigidly attached to each other in the aforementioned manner, the outer surface of the upper section 18 is substantially flush with the outer surface of the central portion 32 of the lower section 24.

Extending proximally from the proximal surface 34 of the central portion 32 in substantially perpendicular relation thereto is an elongate dilator projection portion 40 which is coaxially aligned with the central opening 28 of the upper section 18. The dilator projection portion 40 has a generally cylindrical configuration, and defines a blunt proximal tip 42. In addition to the dilator projection portion 40, formed on the lower section 24 and extending distally from the distal surface 44 of the central portion 32 thereof is an elongate adaptor portion 46. In the injection site 10, the adaptor portion 46 preferably comprises a tubing connection which defines a tapered outer surface and a blunt distal tip 48. Also extending distally from the distal surface 44 of the central portion 32 is a distal lock region 50 which circumvents the adaptor portion 46 and is used to facilitate the connection of the housing 16 to an annular surface. In the preferred embodiment, the distal lock region 50 includes Luer threads 52 formed on its inner surface, and is sized such that the distal tip 48 of the adaptor portion 46 protrudes beyond the distal rim thereof.

As seen in FIG. 4, the adaptor portion 46 is configured to facilitate the connection of the injection site 10 to the fluid line 12. Such connection is achieved by the advancement of the adaptor portion 46 into one end of the lumen of the fluid line 12, with the adaptor portion 46 being sized and configured so as to be frictionally retained therewithin. It will be recognized that the distal lock region 50 may be used to connect the injection site 10 to infusion components other than for the fluid line 12. When the adaptor portion 46 is not being used to facilitate the connection of the injection site 10 to the fluid line 12 or other infusion components, the same is typically covered by a breather cap 54 which has a complementary configuration and is advanced thereover and frictionally maintained thereupon, as seen in FIG. 2. Importantly, the dilator projection and adaptor portions 40, 46 of the lower section 24 collectively define an elongate fluid passage 56 which extends through the lower section 24 and is co-axially aligned with the central opening 28 of the upper section 18.

Referring now to FIGS. 3–5, the injection site 10 constructed in accordance with the present invention further comprises a reseal member 58 which is disposed within the central opening 28 and interior chamber 26 of the housing 16. The reseal member 58 comprises a resilient body 60 having a generally cylindrical proximal portion 62 which defines a proximal end 64, and a generally cylindrical distal portion 66 which defines a distal end 68. Disposed between the proximal and distal portions 62, 66 is a cylindrically configured middle portion 70. The proximal, middle and distal portions 62, 70, 66 are of progressively increasing diameter, with the diameter of the distal portion 66 exceeding that of the middle portion 70, and the diameter of the middle portion 70 exceeding that of the proximal portion 72. The transition between the proximal and middle portions 62, 70 is defined by a first beveled shoulder 72, with the transition between the middle and distal portions 70, 66 being defined by a second beveled shoulder 74.

The proximal end 64 of the body 60 defines a recessed, circularly configured outer surface 76 which has a generally planar configuration. In addition to the outer surface 76, the proximal end 64 defines a generally semi-spherical inner surface 78. Extending axially through the proximal end 64 from the outer surface 76 to the apex of the inner surface 78 is an aperture 80. Additionally, formed about and extending radially inward from the distal end 68 of the body 60 is a continuous annular flange 82, the inner peripheral edge of which defines an enlarged bead. The body 60 is preferably fabricated from silicone, though the same may alternatively be fabricated from a similar resilient material such as rubber.

The reseal member further comprises a radial leaf spring 84 which is disposed within the body 60. The radial leaf spring 84 comprises a generally cylindrical base portion 86 which transitions into three (3) identically configured, equidistantly spaced leaf portions 88 via a beveled shoulder 90. The leaf portions 88 are separated from each other by three (3) longitudinally extending slots 92 which extend to the shoulder 90. Formed on the inner surfaces of respective ones of the leaf portions 88 are generally wedge-shaped ramps 94, the use of which will be discussed in more detail below.

As best seen in FIGS. 3 and 4, the radial leaf spring 84 is disposed within the body 60 in a manner wherein the outermost ends of the leaf portions 88 are received into an annular channel circumventing the semi-spherical inner surface 78 of the proximal end 64. Additionally, the distal portion 66 of the body 60 is wrapped about the base portion 86 of the radial leaf spring 84 such that the flange 82, and in particular its bead, extends about the inner surface thereof. The radial leaf spring 84 is preferably fabricated from polysulfone or polycarbonate, though similar rigid materials with memory may be utilized as an alternative.

In addition to the body 60 and radial leaf spring 84, the reseal member 58 of the injection site 10 comprises an elongate, generally cylindrical axial doughnut spring 96 which has a splined outer surface and includes a bore 98 extending longitudinally (i.e., axially) therethrough. As will be discussed in more detail below, the doughnut spring 96 defines a first or proximal end which is normally abutted against the distal end 68 of the body 60, and a second or distal end which is normally abutted against the housing 16, and in particular the proximal surface 34 of the central portion 32 of the lower section 24. Like the body 60, the doughnut spring 96 is preferably fabricated from silicone, though the same may alternatively be fabricated from a similar resilient material such as rubber.

In the injection site 10, the aperture 80 extending through the proximal end 64 of the body 60 is elastically openable and closable. In this respect, the reseal member 58 of the injection site 10 normally resides in a first position within the housing 16 (shown in FIG. 3) wherein the aperture 80 is in a closed configuration. Importantly, the reseal member 58 is selectively deformable such that the application of distally directed pressure thereto, and in particular the raised lip circumventing the outer surface 76 of the proximal end 64, will cause the same to distally advance within the housing 16 to a second position (shown in FIG. 4) wherein the aperture 80 assumes an open configuration. As will be discussed in more detail below, due to the resiliency of the reseal member 58, and in particular the doughnut spring 96 thereof, the removal of the distally directed pressure from the proximal end 64 will cause the reseal member 58 to resiliently return to its first position wherein the aperture 80 reassumes the closed configuration.

When the reseal member 58 is disposed in its normal, first position within the housing 16, the dilator projection portion 40 of the lower section 24 is extended through the bore 98 of the doughnut spring 96 and into the hollow interior of the radial leaf spring 84. In this respect, the proximal tip 42 of the dilator projection portion 40 extends to approximately the beveled shoulder 90 of the radial leaf spring 84. When extended into the radial leaf spring 84, the dilator projection portion 40 passes through the opening defined by the annular flange 82 of the body 60, and in particular the bead defined thereby. Importantly, the diameter of the opening defined by this bead is less than the outer diameter of the dilator projection portion 40. As such, when the dilator projection portion 40 passes through this opening, the bead is sealed in a fluid-tight manner against the outer surface thereof, i.e., the bead is compressed between the outer surface of the dilator projection portion 40 and the inner surface of the base portion 86 of the radial leaf spring 84.

Additionally, when the reseal member 58 is in its first position, both the proximal and middle portions 62, 70 of the body 60 reside within the central opening 28 of the upper section 18, with the second beveled shoulder 74 and distal portion 66 of the body 60, as well as the doughnut spring 96, residing within the interior chamber 26 of the housing 16. Importantly, though the diameter of the middle portion 70 of the body 60 exceeds the diameter of the proximal portion 62 thereof, both the proximal and middle portions 62, 70 extend along and cover the outer surfaces of the leaf portions 88 when the reseal member 58 is in its first position. In this respect, due to the middle portion 70 being disposed within the central opening 28, the same is collapsed (i.e., compressed) against the outer surfaces of the leaf portions 88, thereby "flattening" the first beveled shoulder 72 normally defined between the proximal and middle portions 62, 70. When the reseal member 58 is in its first position, the second beveled shoulder 74 of the body 64 extends along and covers the shoulder 90 of the radial leaf spring 84, and is compressed between the shoulder 90 and the inclined shoulder 30 formed in the inner surface of the upper section 18. Additionally, the proximal end 64 of the body 60 protrudes slightly beyond the rim of the proximal portion 20 of the upper section 18, as best seen in FIGS. 2 and 3.

As previously indicated, the proximal end of the doughnut spring 96 is abutted against the distal end 68 of the body 60, with the distal end of the doughnut spring 96 being abutted against the central portion 32 of the lower section 24, and in particular the proximal surface 34 thereof. Importantly, in the injection site 10, the distance separating the shoulder 30 from the proximal surface 34 of the central portion 32 is slightly less than the combined length of the distal portion 66 of the body 60 and doughnut spring 96. Thus, when the reseal member 58 is disposed in its first position within the housing 16, the doughnut spring 96 is slightly compressed between the distal end 68 of the body 60 and the proximal surface 34 of the central portion 32, thus applying a pre-load thereto which causes the same to bulge slightly outwardly as shown in FIG. 3. Due to the application of the pre-load thereto, the doughnut spring 96 is operable to force the middle portion 70 of the body 60 upwardly into the central opening 28, thus collapsing the same in the aforementioned manner and facilitating the compression of the second beveled shoulder 74 between the shoulders 30, 90.

Importantly, when the reseal member 58 is in its first position, the leaf portions 88 of the radial leaf spring 84 apply a radially inward biasing force to the proximal end 64 of the body 60 which maintains the aperture 80 in its closed configuration.

As seen in FIG. 4, the application of distally directed pressure to the proximal end 64 of the body 60 by an infusion component such as the tip 15 of the introducer 14 causes the radial leaf spring 84 to be distally advanced over the dilator projection portion 40. Such advancement removes the second beveled shoulder 74 of the body 60 from its abutting contact with the shoulder 30, and further forces the middle portion 70 of the body 60 from within the central opening 28. Additionally, such distal advancement facilitates the compression of the doughnut spring 96, thus causing the same to bulge outwardly within the interior chamber 26 of the housing 16. Importantly, the camming action of the dilator projection portion 40 against the leaf portions 88, and in particular the ramps 94 formed on the inner surfaces thereof, causes the same to be flexed outwardly, thus facilitating the radial expansion of the aperture 80 to its open configuration.

Additionally, since the middle portion 70 of the body 60 is removed from within the constricting central opening 28 of the upper section 18, the same resiliently returns to its normal orientation (shown in FIG. 5), thereby forming the first beveled shoulder 72 and defining an expandable and collapsible reservoir 100 between the inner surface of the middle portion 70 and the outer surfaces of the leaf portions 88 and shoulder 90 of the radial leaf spring 84. Thus, when the reseal member 58 is moved to its second position as shown in FIG. 4, the proximal portion 62 of the body 60 extends along and covers the outer surfaces of the leaf portions 88, with the distal portion 66 extending along and covering the base portion 86 of the radial leaf spring 84. However, the middle portion 70 of the body 60 is spaced from the outer surfaces of the leaf portions 88, thus defining the reservoir 100. In this respect, only the proximal portion 62 of the body 60 resides within the central opening 28, with the middle and distal portions 70, 66 of the body 60 and the fully compressed doughnut spring 96 residing within the interior chamber 26.

When the reseal member 58 of the injection site 10 is moved to its second position as shown in FIG. 4, the open aperture 80 communicates with both the fluid passage 56 and the reservoir 100. In particular, the open aperture 80 is co-axially aligned with the fluid passage 56, thus creating a continuous flow path between the introducer 14, the fluid passage 56, and the infusion component (such as the fluid line 12) to which the adaptor portion 46 is connected. The open aperture 80 fluidly communicates with the reservoir 100 via the slots 92 extending between the leaf portions 88 of the radial leaf spring 84. As such, a medicament dispensed from the introducer 14 flows through the open aperture 80, and into the fluid passage 56 and reservoir 100. Importantly, the medicament expelled from the introducer 14 is prevented from leaking into the interior chamber 26 by the seal created by the abutment of the tip 15 of the introducer 14 against the raised lip circumventing the outer surface 76 of the proximal end 64, and by the seal created by the compression of the flange 82 between the dilator projection portion 40 and base portion 86 of the radial leaf spring 84. As will be recognized, the seal created by the flange 82 is a sliding seal which travels longitudinally along the dilator projection portion 40 as the reseal member 58 is advanced to its second position.

Due to the resiliency of the doughnut spring 96, the removal of the distally directed pressure from the proximal end 64 causes the radial leaf spring 84 to be proximally withdrawn from over the dilator projection portion 40, thus facilitating the resilient return of the reseal member 58 to its first position, as shown in FIG. 3. The return of the reseal member 58 to its first position causes the aperture 80 to resiliently return to its closed configuration. Additionally, as the reseal member 58 moves toward its first position, the resultant forcing of the middle portion 70 of the body 60 into the central opening 28 facilitates the collapse of the reservoir 100 since, as previously explained, the middle portion 70 is compressed against the outer surfaces of the leaf portions 88 when the reseal member 58 is in its first position. Importantly, this collapse of the reservoir 100 causes the fluid previously introduced thereinto to be expelled from therewithin and into the fluid passage 56 via the slots 92 extending between the leaf portions 88 of the radial leaf spring 84. The advantages attendant to this resultant flow of fluid into the fluid passage 56 during the return of the reseal member 58 to its first position will be discussed in more detail below.

As previously explained, in prior art needleless injection sites there is a tendency for blood to be drawn into the fluid line extending into the anatomical passage when the introducer is withdrawn from within the injection site. Such back-flow of blood is attributable to the vacuum created in the fluid line when the introducer is withdrawn from within the prior art injection site. Advantageously, the collapse of the reservoir 100 of the injection site 10 in the aforementioned manner prevents a vacuum from being created within the fluid line 12 when the reseal member 58 moves from its second position (shown in FIG. 4) to its first position (shown in FIG. 3). In this respect, the flow of fluid from the reservoir 100 into the fluid passage 56 creates zero or positive pressure within the fluid passage 56 and fluid line 12 coupled thereto, thus preventing blood from being drawn thereinto. Advantageously, the absence of blood within the fluid line 12 prevents any undesirable coagulation therewithin, and eliminates the risk of inadvertent obstruction of the fluid line 12.

In the injection site 10, the reservoir 100 is sized so as to displace a volume of fluid which is equal to or greater than the product of the mean internal diameter of the fluid passage 56 extending through the dilator projection portion 40 and the distance of axial travel of the reseal member 58 between its first and second positions. For most applications, the expanded reservoir 100 is sized having a volumetric capacity of approximately 0.035 ml which is sufficient to facilitate zero or positive pressure within the fluid passage 56 when the reseal member 58 is returned to its first position. It will be recognized that increasing the diameter of the middle portion 70 of the body 60 facilitates a resultant increase in the volumetric capacity of the reservoir 100. In this respect, an increase in the volume of the reservoir 100 causes positive pressure to be created within the fluid passage 56 when the reservoir 100 is collapsed. Conversely, the diameter of the middle portion 70 may be reduced such that the volume of the reservoir 100 causes zero pressure to be created in the fluid passage 56 when the reservoir 100 is collapsed. As previously explained, the injection site 10 shown in FIGS. 2–4, and in particular the housing 16 thereof, is adapted to be fluidly connected to the fluid line 12. Though not shown, it will be recognized that the housing 16 may be configured for connection to other infusion components as well. In this respect, other injection sites may be fabricated which include the reseal member 58 incorporated into a differently configured housing without departing from the spirit and scope of the present invention. Indeed, any housing with which the reseal member 58 is utilized need only be configured such that the reseal member 58 is movable between its first and second positions to create the fluid passage from the introducer 14 into the infusion component in the previously described manner.

Due to the configuration of the reseal member 58, in an emergency situation a medicament may be passed into the fluid passage 56 via a needled introducer device rather than through the non-needled introducer 14 previously described. In this respect, when a needled introducer device is utilized, the reseal member 58 will not be moved to its second position to facilitate the opening of the aperture 80. Rather, the needle of the needled introducer device is simply forced through the closed aperture 80 and into the fluid passage 56 of the dilator projection portion 40.

Figure 6:
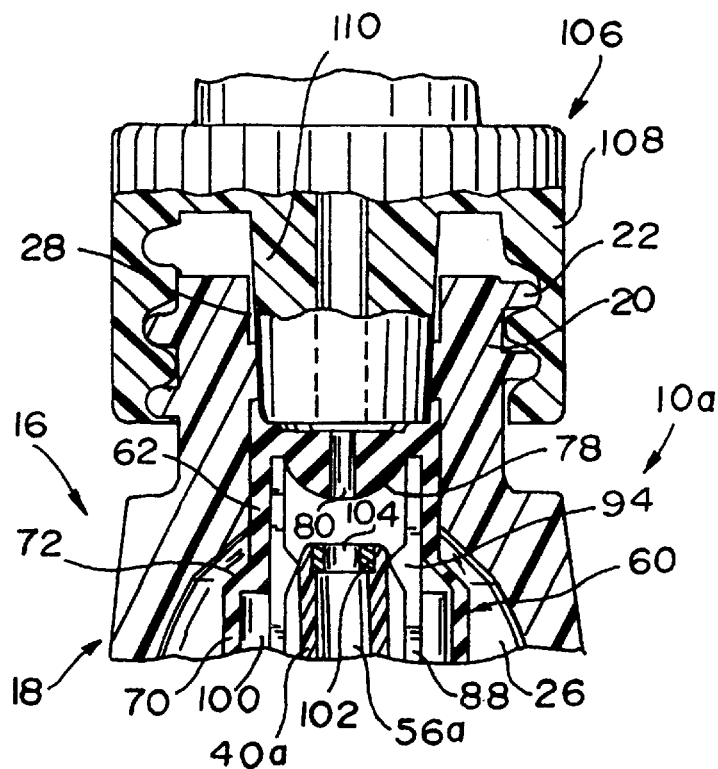
FIG. 6 is a partial cross-sectional view of a fixed flow rate needleless injection site constructed in accordance with a second embodiment of the present invention.

Referring now to FIG. 6, there is shown a fixed flow rate needleless injection site 10a constructed in accordance with a second, preferred embodiment of the present invention. The injection site 10a is substantially similar in construction and function to the previously described injection site 10. However, the injection site 10a of the second embodiment is further adapted to provide a fixed rate of flow of a therapeutic fluid therethrough when fluidly coupled within an I.V. drip unit. In this respect, the injection site 10a, in addition to providing the previously discussed advantages and benefits associated with the injection site 10, is further adapted for use as a rate controlling device for regulating the flow of a therapeutic fluid through an I.V. drip unit.

As seen in FIG. 6, the injection site 10a is structurally identical to the previously described injection site 10, except that disposed within the proximal end of the dilator projection portion 40a of the injection site 10a is an annular metering member 102. More particularly, the metering member 102 resides within the proximal end of the fluid passage 56a of the dilator projection portion 40a. The metering member 102 defines proximal and distal surfaces, with the proximal surface being substantially flush with the proximal end of the dilator projection portion 40a, and the distal surface resting upon an annular shoulder formed within the inner surface of the dilator projection portion 40a which defines the fluid passage 56a. The preferred thickness of the metering member 102 (i.e., the distance separating the opposed proximal and distal surfaces thereof) is from approximately 1 mm to 10 mm.

Centrally positioned within the metering member 102 (i.e., extending axially therethrough) is an orifice 104. The orifice 104 has a preferred diameter of approximately 300 microns, though other sizes thereof, as well as other thicknesses of the metering member 102, are contemplated herein for reasons which will be discussed in more detail below. The metering member 102 may comprise a separate element which is secured within the fluid passage 56a via an adhesive or other attachment process, or may alternatively be integrally formed as part of the dilator projection portion 40a.

When the reseal member 58 of the injection site 10a is actuated to its second position as shown in FIG. 6, the open aperture 80 fluidly communicates with the fluid passage 56a of the dilator projection portion 40a via the orifice 104 of the metering member 102. As such, the metering member 102, and in particular the orifice 104 thereof, controls the rate at which fluid is able to flow into the fluid passage 56a, and hence through the injection site 10a. As will be recognized, the rate of fluid flow through the metering member 102 may be altered by changing the diameter of the orifice 104 and/or the thickness of the metering member 102. In this respect, it is contemplated that metering members 102 of differing thicknesses and/or including orifices 104 of differing diameters may be incorporated into the injection site 10a depending on the desired rate of fluid flow to be achieved therethrough. It is further contemplated that the upper section 18 of the housing 16 may be fabricated to have one of a wide variety of different colors, with each particular color corresponding to a particular size metering member 102, and hence a particular rate of fluid flow which can be achieved through the injection site 10a.

As further seen in FIG. 6, when the injection site 10a is to be used as a flow rate controlling device, a Luer connector 106 is typically employed to facilitate the connection of one end of a tubular fluid line to the housing 16, with the opposite end of such fluid line being fluidly coupled to a solution bag. The Luer connector 106 includes an internally threaded lock section 108 which threadably engages the externally threaded proximal portion 20 of the upper section 18. In addition to the lock section 108, the Luer connector 106 includes a frusto-conical tip section 110 which, when the lock section 108 is engaged to the upper section 18, is adapted to facilitate the distal advancement of the reseal member 58 of the injection site 10a from its first position to its second position.

Referring now to FIGS. 7, 7a and 7b, there is depicted a reseal member 58a which may be used in the injection sites 10, 10a as an alternative to the previously described reseal member 58. The reseal member 58a comprises a resilient body 60a having a distal end 68a and a proximal end 64a which, as best seen in FIG. 7a, defines an inner surface 78a and an outer surface 76a. Extending through the proximal end 64a between the inner and outer surfaces 78a, 76a thereof is an elastically openable and closable aperture 80a. The proximal end 64a of the body 60a is defined by a generally cylindrical proximal portion 62a thereof, with the distal end 68a being defined by a generally cylindrical distal portion 66a of the body 60a. The proximal and distal portion 62a, 66a are separated by a beveled shoulder 73a formed therebetween, and are sized such that diameter of the distal portion 66a exceeds the diameter of the proximal portion 62a.

In the reseal member 58a, the inner surface 78a of the proximal end 64a has a generally semi-spherical configuration to prevent any inadvertant tearing of the proximal end 64a when the reseal member 58a is moved between its first and second positions. Additionally, preferably formed in the outer surface 76a of the proximal end 64a is a circularly configured depression 112a which is centrally positioned within the outer surface 76a. The aperture 80a of the reseal member 58a extends axially between the approximate center of the depression 112a and the apex of the semi-spherical inner surface 78a. The formation of the depression 112a within the outer surface 76a causes distally directed compressive pressure exerted against the proximal end 64a by the tip 15 of the introducer 14 to be applied to the periphery of the outer surface 76a about the aperture 80a. Such peripheral application of compressive pressure eliminates axial bulge of the proximal end 64a of the body 60a during the movement of the reseal member 58a from its first position to its second position. Such axial bulge, if not prevented, could obstruct flow through the aperture 80a of the reseal member 58a.

As further seen in FIGS. 7 and 7a, formed on the proximal portion 62a of the body 60a is a centering ring 114a which extends thereabout and has a generally wedge-shaped cross-sectional configuration. The centering ring 114a travels along the surface of the upper section 18 which defines the central opening 28 as the reseal member 58a moves between its first and second positions and maintains the aperture 80a in coaxial alignment with the fluid passage 56 of the dilator projection portion 40. Maintaining such coaxial alignment insures that the aperture 80a will elastically expand to its open position when the reseal member 58a is distally advanced within the housing 16 to its second position. Though traveling along the surface of the upper section 18 defining the central opening 28, the center ring 114a does not create a fluid-tight seal thereagainst. In this respect, as will be discussed in more detail below, the centering ring 114a and/or upper section 18 are preferably provided with flow passages which maintain the interior chamber 26 of the housing 16 in fluid communication with ambient air during the movement of the reseal member 58a between its first and second positions.

In addition to the formation of the centering ring 114a upon the proximal portion 62a of the body 60a, preferably formed on the distal portion 66a of the body 60a adjacent the beveled shoulder 73a is at least one, and preferably a pair of compression rings 116a which extend thereabout. Like the centering ring 114a, each of the compression rings 116a preferably has a generally wedge-shaped cross-sectional configuration. The compression rings 116a effectively increase the diameter of the distal portion 66a of the reseal member 58a for reasons which will be discussed in more detail below.

Referring now to FIGS. 8a and 8b, as an alternative to the compression rings 116a, the distal portion 66a of the body 60a may include at least one, and preferably two sets of arcuately contoured compression tabs 118a which are formed thereon and extend thereabout adjacent the beveled shoulder 73a of the body 60a. Each set preferably comprises four compression tabs 118a which are separated by intervals of approximately 90 degrees. The compression tabs 118a of each set are preferably in longitudinal alignment with respective ones of the compression tabs 118a of the other set.

Referring now to FIGS. 8c and 8d, as a further alternative to the compression rings 116a, the distal portion 66a of the body 60a may include a plurality of elongate, longitudinally extending compression ribs 120a formed thereon such that the proximal ends of the compression ribs 120 are adjacent the beveled shoulder 73a of the body 60a. The compression ribs 120a each preferably have a generally wedge-shaped cross-sectional configuration, and extend about the distal portion 66a of the body 60a in equidistantly spaced relation to each other. Due to the longitudinal orientation of the compression ribs 120a upon the distal portion 66a, they extend in generally parallel relation to the axis of the body 60a of the reseal member 58a. The compression tabs 118a and compression ribs 120a, like the compression rings 116a, are used to increase the diameter of the distal portion 66a.

In addition to either the compression rings 116a, compression tabs 118a, or compression ribs 120a, formed on the distal portion 66a is an annular flange 122a which extends about and radially inward from the distal end 68a of the body 60a. Formed on the inner peripheral edge of the flange 122a is an enlarged bead 124a. The flange 122a, and in particular the bead 124a thereof, is used to form a seal against the dilator projection portion 40 when the reseal member 58a is inserted into the interior of the housing 16. The seal formed by the bead 124a is maintained during the movement of the body 60a along the dilator projection portion 40 as the reseal member 58a is moved between its first and second positions.

The reseal member 58a further comprises a radial leaf spring 84a which is disposed within the body 58a. The radial leaf spring 84a comprises a generally cylindrical base portion 86a which transitions into three (3) identically configured, equidistantly spaced leaf portions 88a via a beveled shoulder 90a. The leaf portions 88a are separated from each other by three (3) longitudinally extending slots 92a which extend to the shoulder 90a. Formed on the inner surfaces of respective ones of the leaf portions 88a are downwardly sloping, generally wedge-shaped ramps 94a which extend to the base portion 86a. The use of the ramps 94a will also be discussed in more detail below.

The radial leaf spring 84a is disposed within the body 60a in a manner wherein the outermost ends of the leaf portions 88a are received into an annular channel 126a circumventing the semi-spherical inner surface 78a of the proximal end 64a. Additionally, the distal end 68a of the body 60a is wrapped about the base portion 86a of the radial leaf spring 84a such that the bead 124a extends about the inner surface thereof. The radial leaf spring 84a is preferably fabricated from polysulfone or polycarbonate, though similar rigid materials with memory may be utilized as an alternative.

When the radial leaf spring 84a is inserted into the body 60a in the aforementioned manner, the proximal portion 62a of the body 60a extends along and covers the outer surfaces of the leaf portions 88a. However, due to the inclusion of the beveled shoulder 73a within the body 60a, a section of the distal portion 66a is spaced from the outer surfaces of the leaf portions 88a, with an annular reservoir similar to the previously described reservoir 100 being defined therebetween. However, a reduced diameter wall segment 128a formed on the inner surface of the distal portion 66a adjacent the flange 122a is abutted against and covers the outer surface of the base portion 86a of the radial leaf spring 84a. The reservoir of the reseal member 58a is placed into fluid communication with the interior of the radial leaf spring 84a via the slots 92a defined between the leaf portions 88a thereof.

Referring now to FIGS. 7, 7b and 7c, in addition to the body 60a and radial leaf spring 84a, the reseal member 58a comprises an elongate, generally cylindrical axial doughnut spring 96a which has a splined or fluted outer surface and includes a bore 98a extending longitudinally (i.e., axially) therethrough. The splined outer surface of the doughnut spring 96a defines a plurality of elongate channels extending longitudinally therewithin. As will be discussed in more detail below, the splined configuration of the doughnut spring 96a assists in the return of the reseal member 58a to its first position subsequent to the removal of the distally directed pressure therefrom. The doughnut spring 96a includes a first or proximal end which is chamfered and defines an annular contact surface 99a which circumvents the bore 98a and is normally abutted against the distal end 68a of the body 60a. The doughnut spring 96a also includes a second or distal end which is normally abutted against the housing 16, and in particular the proximal surface 34 of the central portion 32 of the lower section 24. In the reseal member 58a, both the body 60a and the doughnut spring 96a are preferably fabricated from silicone or similar resilient materials such as rubber.

The reseal member 58a functions in a manner which is closely similar to that of the previously described reseal member 58. In this respect, when the reseal member 58a is inserted into the interior of the housing 16, it normally resides in its first position wherein the elastically openable and closable aperture 80a is closed. The application of distally directed compressive pressure to the periphery of the outer surface 76a of the proximal end 64a facilitates the distal advancement of the reseal member 58a within the housing 16 to its second position wherein the aperture 80a is opened. The resiliency of the reseal member 58a, and in particular its doughnut spring 96a, causes the reseal member 58a to resiliently return to its first position wherein the aperture 80a is closed upon the removal of the distally directed compressive pressure from the proximal end 64a of the body 60a.

When the reseal member 58a is disposed in its normal, first position within the housing 16, the dilator projection portion 40 is extended through the bore 98a of the doughnut spring 96a and into the hollow interior of the radial leaf spring 84a. In this respect, the proximal tip 42 of the dilator projection portion 40 extends to approximately the beveled shoulder 90a of the radial leaf spring 84a. When extended into the radial leaf spring 84a, the dilator projection portion 40 passes through the opening defined by the flange 122a of the body 60a, and in particular the bead 124a defined thereby. The diameter of the opening defined by the bead 124a is less than the outer diameter of the dilator projection portion 40. As such, when the dilator projection portion 40 passes through this opening, the bead 124a is sealed in a fluid-tight manner against the outer surface thereof, i.e., the bead 124a is compressed between the outer surface of the dilator projection portion 40 and the inner surface of the base portion 86a of the radial leaf spring 84a.

When the reseal member 58a is in its first position, the proximal portion 62a, beveled shoulder 73a, and that section of the distal portion 66a extending proximally from the reduced diameter wall segment 128a reside within the central opening 28 of the upper section 18. In this respect, only that section of the distal portion 66a including the wall segment 128a formed thereon and the distal end 68a of the body 60a reside within the interior chamber 26 of the housing 16. This orientation of the reseal member 58a when in its first position results in the "flattening" of the beveled shoulder 73a and the compression of that section of the distal portion 66a normally spaced from the leaf portions 88a against the outer surfaces thereof. As will be recognized, the compression of the distal portion 66a against the leaf portions 88a results in the collapse of the reservoir 100a normally defined therebetween. When the reseal member 58a is in its first position, the beveled shoulder 90a of the radial leaf spring 84a engages the inclined shoulder 30 formed in the inner surface of the upper section 18, with a section of the distal portion 66a of the body 60a being compressed therebetween. Additionally, the proximal end 64a of the body 60a protrudes slightly beyond the rim of the proximal portion 20 of the upper section 18.

As previously indicated, the proximal end of the doughnut spring 96a is abutted against the distal end 68a of the body 60a, with the distal end of the doughnut spring 96a being abutted against the central portion 32 of the lower section 24, and in particular the proximal portion 34 thereof. When the reseal member 58a is in its first position, the distance separating the shoulder 30 from the proximal surface 34 is slightly less than the combined length of the doughnut spring 96a and that section of the distal portion 66a of the body 60a residing in the interior chamber 26. As such, the doughnut spring 96a is slightly compressed between the distal end 68a of the body 60a and the proximal surface 34 of the central portion 32, thus applying a pre-load thereto which causes the same to bulge slightly outwardly. Due to the application of the pre-load thereto, the doughnut spring 96a is operable to force the body 60a upwardly into the central opening 28 in the aforementioned manner, thus facilitating the flattening of the beveled shoulder 73a and the collapse of the reservoir of the reseal member 58a. When the reseal member 58a is in its first position, the leaf portions 88a of the radial leaf spring 84a apply a radially inward biasing force to the proximal end 64a of the body 60a which normally closes the aperture 80a when no distally directed compressive pressure is applied to the outer surface 76a of the proximal end 64a.

The application of distally directed compressive pressure to the proximal end 64a of the body 60a by the tip 15 of the introducer 14 causes the radial leaf spring 84a to be distally advanced over the dilator projection portion 40. Such advancement removes the beveled shoulder 90a of the radial leaf spring 84a from its engagement to the shoulder 30, and further forces the section of the distal portion 66a proximal to the reduced diameter wall segment 128a as well as the beveled shoulder 73a from within the central opening 28. Such distal advancement also facilitates the compression of the doughnut spring 96a, thus causing the same to bulge outwardly within the interior chamber 26 of the housing 16. The camming action of the dilator projection portion 40 against the leaf portions 88a, and in particular the ramps 94a formed on the inner surfaces thereof, causes the leaf portions 88a to be flexed outwardly, thus facilitating the opening of the aperture 80a via the radial expansion thereof. The sizing of the ramps 94a is adapted to prevent the bowing of the leaf portions 88a as they are flexed outwardly by the distal advancement of the reseal member 58a over the dilator projection portion 40.

As will be recognized, when the reseal member 58a is moved to its second position in the aforementioned manner, the removal of the entire distal portion 66a from within the central opening 28 facilitates the resilient re-forming of both the beveled shoulder 73a and the expandable and collapsible reservoir between the inner surface of the distal portion 66a and the outer surfaces of the leaf portions 88a of the radial leaf spring 84a. Thus, when the reseal member 58a is in its second position, only the proximal portion 62a of the body 60a remains within the central opening 28, with the distal portion 66a and beveled shoulder 73a, as well as the fully compressed doughnut spring 96a, residing within the interior chamber 26. The compression of the doughnut spring 96a during the movement of the reseal member 58a to its second position typically causes the splines on the outer surface of the doughnut spring 96a to assume a generally serpentine configuration as will be discussed in more detail below.

When the reseal member 58a is moved to its second position, the open aperture 80a communicates with both the fluid passage 56 and the expanded reservoir of the reseal member 58a. In particular, the open aperture 80a is coaxially aligned with the fluid passage 56a, thus creating a continuous flow path between the introducer 14, the fluid passage 56, and the infusion component (such as the fluid line 12) to which the adaptor portion 46 is connected. As previously indicated, the open aperture 80 also fluidly communicates with the reservoir of the reseal member 58a via the slots 92a extending between the leaf portions 88a of the radial leaf spring 84a. As such, a medicament dispensed from the introducer 14 flows through the open aperture 80a, and into the fluid passage 56 as well as the expanded reservoir. The medicament expelled from the introducer 14 is prevented from leaking into the interior chamber 26 by the seal created by the abutment of the tip 15 of the introducer 14 against the raised periphery of the outer surface 76a of the proximal end 64a, and by the seal created by the compression of the bead 124a between the dilator projection portion 40 and the base portion 86a of the radial leaf spring 84a. The seal created by the bead 124a is a sliding seal which travels longitudinally along the dilator projection portion 40 as the reseal member 58a is advanced to its second position.

Due to the resiliency of the doughnut spring 96a, the removal of the distally directed compressive pressure from the proximal end 64a causes the radial leaf spring 84a to be proximally withdrawn from over the dilator projection portion 40, thus facilitating the resilient return of the reseal member 58a to it first position, and hence the return of the doughnut spring 96a to its original, pre-loaded configuration. The return of the reseal member 58a to its first position causes the aperture to close, and also results in the beveled shoulder 73a and the section of the distal portion 66a of the body 60a proximal to the reduced diameter wall segment 128a thereof being forced back into the central opening 28. As will be recognized, the forcing of the section of the distal portion 66a of the body 60a normally spaced from the leaf portions 88a back into the central opening 28 facilitates the collapse of the reservoir of the reseal member 58a. This collapse of the reservoir causes the fluid previously introduced thereinto to be expelled from therewithin and into the fluid passage 56 via the slots 92a extending between the leaf portions 88a of the radial leaf spring 84a. As previously explained in relation to the reseal member 58, this resultant flow of fluid into the fluid passage 56 during the return of the reseal member 58a to its first position creates zero or positive pressure within the fluid passage 56 and fluid line 12 coupled thereto, thus preventing blood from being drawn thereinto. The absence of blood within the fluid line 12 prevents any undesirable coagulation therewithin, and eliminates the risk of inadvertant obstruction of the fluid line 12.

The collapse of the reservoir which occurs when the reseal member 58a returns to its first position is assisted by the inclusion of the compression rings 116a, compression tabs 118a, or compression ribs 120a on the distal portion 66a of the body 60a. As indicated above, these structures effectively increase the diameter of the distal portion 66a, thus assisting in the compression thereof against the outer surfaces of the leaf portions 88a and the resultant collapse of the reservoir when that section of the distal portion 66a normally spaced from the leaf portions 88a is forced into the central opening 28. The reservoir of the reseal member 58a is preferably sized so as to displace a volume of fluid which is equal to or greater than the product of the mean internal diameter of the fluid passage 56 extending through the dilator projection portion 40 and the distance of axial travel of the reseal member 58a between its first and second positions. For most applications, the expanded reservoir of the reseal member 58a is sized having a volumetric capacity of approximately 0.035 ml which is sufficient to facilitate zero or positive pressure within the fluid passage 56 when the reseal member 58a is returned to its first position. As with the previously described reseal member 58, the reseal member 58a may be used in conjunction with both needled and non-needled introducers.

As previously indicated, the first end of the doughnut spring 96a is preferably chamfered, with the annular contact surface 99a defined thereby being abutted against the distal end 68a of the body 60a. As such, when the reseal member 58a is moved from its first position to its second position, the compressive pressure exerted by the body 60a and radial leaf spring 84a against the doughnut spring 96a is applied solely to the contact surface 99a of the doughnut spring 96a which is in general longitudinal alignment with the flange 122a of the body 60a, and in particular the bead 124a thereof. The firm engagement between the flange 122a and contact surface 99a when the reseal member is moved to its second position prevents fluids directed into the open reseal member 58a at high pressure from forcing the bead 124a downwardly out of contact with the dilator projection portion 40. The prevention of this downward movement maintains the fluid-tight seal between the bead 124a and the dilator projection portion 40. As such, the chamfered configuration of the first end of the doughnut spring 96a effectively isolates a force on the bead 124a which maintains its sealed engagement to the dilator projection portion 40.

Additionally, as the doughnut spring 96a is compressed during the movement of the reseal member 58a from its first position to its second position, it is also typically twisted due to the twisting of the Luer lock onto the Luer threads 22 of the upper section 18. Such twisting of the doughnut spring 96a causes the splines thereof to assume generally serpentine configurations. This serpentine twisting of the splines of the doughnut spring 96a assists in the rebound thereof and hence the return of the reseal member 58a to its first position subsequent to the removal of the distally directed compressive pressure therefrom. As such, the rebound of the doughnut spring 96a is facilitated not only by its axial compression, but by the serpentine twisting of the splines thereof.

Referring now to FIG. 9, the housing 16 of the injection site 10, 10a including the reseal member 58a may include an alternatively configured upper section 18a. The upper section 18a is similar to the previously described upper section 18, and includes a reduced diameter proximal portion 20a having Luer threads 22a formed on the outer surface thereof. The proximal portion 20a defines a central opening 28a which communicates with the interior chamber 26 defined by the attachment of the upper section 18a to the lower section 24 of the housing 16. In this respect, similar to the upper section 18, the upper section 18a includes an annular, inclined shoulder 30a formed within the inner surface thereof which defines the transition between the central opening 28a and the interior chamber 26.

The primary difference between the upper section 18a and the upper section 18 lies in the formation of at least one, and preferably three elongate slots 130a within the inner surface of the upper section 18a. As seen in FIG. 9, each of the slots 130a defines a first section 132a which is formed in the inner surface portion of the upper section 18a defining the central opening 28a thereof, and extends from just below the end of the proximal portion 20a to the shoulder 30a. The first section 132a is of gradually increasing depth as it advances toward the shoulder 30a. The first section 132a transitions into a second section 134a which is formed in that portion of the inner surface of the upper section 18a defining the shoulder 30a. The second section 134a in turn transitions into a third section 136a which is formed in that portion of the inner surface of the upper section 18a partially defining the interior chamber 26.

Importantly, the slots 130a create air passages from the interior chamber 26 of the housing 16 to ambient air when the reseal member 58a is moved from its first position to its second position. These air passages prevent a pressure build-up within the interior chamber 26 as could adversely affect the ability to deform the reseal member 58a to its second, open position.

Referring now to FIGS. 10 and 10a, as an alternative to providing the housing 16 with the upper section 18a, the venting of the interior chamber 26 may be accomplished by providing the housing 16 with an alternative lower section 24a. The lower section 24a, if included in the housing 16, would typically not be used in conjunction with the upper section 18a, but rather would be attached to the previously described upper section 18 for purposes of defining the interior chamber 26. The lower section 24a is substantially identical to the previously described lower section 24 and includes a central portion 32a which defines a generally planar, circularly configured proximal surface circumvented by an annular flange portion 36a. The dilator projection portion 40 extends axially from the proximal surface of the central portion 32a. The central portion 32a further defines a circularly configured distal surface 44a which includes an elongate adaptor portion 46a extending axially therefrom and communicating with the dilator projection portion 40. Also extending from the distal surface 44a of the central portion 32a is a distal lock region 50a which circumvents the adaptor portion 46a and is used to facilitate the connection of the housing 16 to an annular surface. As in the lower section 24, in the lower section 24a, the distal tip of the adaptor portion 46a protrudes beyond the distal rim of the distal lock region 50a.

The primary difference between the lower section 24a and the previously described lower section 24 lies in the inclusion of a pair of apertures 138a within the central portion 32a which extend therethrough. In this respect, when the housing 16 including the lower section 24a is assembled, the apertures 138a communicate with and define air passages between the interior chamber 26 and the space defined between the adaptor portion 46a and distal lock region 50a. The apertures 138a provide the same venting function as the slots 130a of the alternative upper section 18a, and prevent a pressure build-up within the interior chamber 26 when the reseal member 58a moves from its first position to its second position. Importantly, as best seen in FIG. 10a, the apertures 138a are not each oriented upon an axis which bisects the axis of the adaptor portion 46a. Rather, one of the apertures 138a is off-set from such axis which ensures that both apertures 138a will not be obstructed by the splines of the doughnut spring 96a at the same time.

Referring now to FIG. 11, rather than providing the housing 16 with the modified upper section 18a and/or modified lower section 24a to facilitate the venting of the interior chamber 26, the centering ring 114a of the body 60a of the reseal member 58a may be provided with one, and preferably three notches 140a therein. These notches 140a create gaps between the outer surface of the proximal portion 62a and inner surface of the upper section 18 defining the central opening 28, and thus define air passages between the interior chamber 26 and ambient air as the reseal member 58a moves from its first position to its second position.

In the injection sites 10, 10a including either of the reseal members 58, 58a, the injection sites 10, 10a function in a manner wherein fluid flows through the reseal member 58, 58a rather than over or around the reseal member 58, 58a. In this respect, the tip 15 of the introducer 14 or tip section 110 of the Luer connector 106 is maintained in sealed engagement to the periphery of the outer surface 76, 76a of the reseal member 58, 58a when the same is distally advanced to its second position. Due to the seal created between the tip 15, 110 against the outer surface 76, 76a, fluid flows directly from the introducer 14 or Luer connector 106 into the aperture 80, 80a which is opened as a result of the movement of the reseal member 58, 58a to its second position, and is prevented from flowing between the inner surface of the upper section 18, 18a of the housing 16 and the reseal member 58, 58a.

In view of the fluid flowing through rather than over or around the reseal member 58, 58a, there is no requirement in the injection sites 10, 10a for any fluid-tight seal to be maintained between any portion of the inner surface of the upper section 18, 18a of the housing 16 and the reseal member 58, 58a. Thus, the modified upper section 18a may be provided with the slots 130a and/or the centering ring 114a provided with the notches 140a for purposes of venting the interior chamber 26 of the housing 16. Additionally, the modified lower section 24a may be provided with the apertures 138a to facilitate the venting of the interior chamber 26 since that portion thereof between the reseal member 58, 58a and upper section 18, 18a is never filled with a fluid.

Additional modifications and improvements of the present invention may also be apparent to those skilled in the art. Thus, the particular combination of parts described and illustrated herein is intended to represent only one embodiment of the present invention, and is not intended to serve as limitations of alternative devices within the spirit and scope of the invention.

What is claimed is:

1. A needleless injection site, comprising:

a housing defining a fluid passage;

a reseal member disposed within the housing and including an openable and closable aperture and an expandable and collapsible reservoir which is adapted to retain a volume of fluid when expanded, said reseal member normally residing in a first position within the housing wherein the aperture is closed and the reservoir is collapsed;

said reseal member being deformable such that the application of compressive pressure thereto will facilitate the movement thereof within the housing to a second position wherein the reservoir is expanded and the aperture is opened and placed into fluid communication with the fluid passage and the reservoir, and the removal of the compressive pressure therefrom will facilitate the resilient return thereof to the first position wherein the aperture is closed and the reservoir is collapsed;

said reseal member being cooperatively engaged to the housing such that the collapse of the reservoir which occurs when the reseal member resiliently returns to the first position forces any volume of fluid retained within the reservoir into the fluid passage for purposes of preventing the creation of a vacuum therewithin.

2. The injection site of claim 1 wherein the fluid passage has an internal diameter and the reservoir, when expanded, has a volumetric capacity which is not less than the product of the internal diameter of the fluid passage and the distance of movement of the reseal member from the first position to the second position.

3. The injection site of claim 2 wherein the volumetric capacity of the expanded reservoir is approximately 0.035 ml.

4. The injection site of claim 1 wherein said reseal member comprises:

a resilient body having a distal end and a proximal end which defines inner and outer surfaces, said aperture extending through the proximal end between the inner and outer surfaces thereof; and a radial leaf spring disposed within said body and adapted to apply a radially inward biasing force to the proximal end which normally closes the aperture when no compressive pressure is applied to the outer surface of the proximal end, said reservoir being defined between the radial leaf spring and the body.

5. The injection site of claim 4 wherein the body of the reseal member includes a centering ring for maintaining the aperture in coaxial alignment with the fluid passage when the reseal member is moved between the first and second positions.

6. The injection site of claim 4 wherein the body of the reseal member includes at least one compression ring to assist in collapsing the reservoir when the reseal member moves from the second position to the first position.

7. The injection site of claim 4 wherein the body of the reseal member includes at least one set of arcuately contoured compression tabs to assist in collapsing the reservoir when the reseal member moves from the second position to the first position.

8. The injection site of claim 4 wherein the body of the reseal member includes a plurality of elongate compression ribs to assist in collapsing the reservoir when the reseal member moves from the second position to the first position.

9. The injection site of claim 4 wherein the outer surface of the proximal end of the body includes a depression formed therein for eliminating axial bulge of the proximal end during the movement of the reseal member from the first position to the second position.

10. The injection site of claim 4 wherein the inner surface of the proximal end of the body has a generally semi-spherical configuration and said aperture extends axially between the outer surface of the proximal end and the apex of the inner surface thereof.

11. The injection site of claim 4 wherein said radial leaf spring comprises a base portion and a plurality of leaf portions which extend from said base portion and include slots therebetween, said leaf portions applying a radially inward biasing force to the proximal end of the body which normally closes the aperture, and said slots defining fluid-flow channels between the aperture and the reservoir when the reseal member is moved to the second position, and between the reservoir and the fluid passage during the return of the reseal member to the first position.

12. The injection site of claim 11 wherein each of the leaf portions includes an inner surface having a ramp formed thereon which extends to the base portion.

13. The injection site of claim 4 wherein said reseal member further comprises an elongate doughnut spring which includes a splined outer surface and is abutted against the distal end of the body and the housing.

14. The injection site of claim 13 wherein the body and the doughnut spring are each fabricated from silicone.

15. The injection site of claim 1 wherein said housing comprises:
an interior chamber;
a central opening which communicates with the interior chamber; and
an elongate, proximally extending dilator projection portion which defines the fluid passage;
said reseal member being disposed within said central opening and said interior chamber.

16. The injection site of claim 15 wherein the housing includes at least one elongate slot disposed therein for venting the interior chamber during the movement of the reseal member from the first position to the second position.

17. The injection site of claim 15 wherein the housing includes at least two apertures disposed therein for venting the interior chamber during the movement of the reseal member from the first position to the second position.

18. The injection site of claim 15 wherein said reseal member comprises:
a resilient body having a distal end and a proximal end which defines inner and outer surfaces, said aperture extending through the proximal end between the inner and outer surfaces thereof;
a radial leaf spring disposed within said body and adapted to apply a radially inward biasing force to the proximal end which normally closes the aperture when no compressive pressure is applied to the outer surface of the proximal end, said reservoir being defined between the radial leaf spring and the body; and
an elongate doughnut spring having a first end which is abutted against the distal end of the body, a second end which is abutted against the housing, and a bore extending longitudinally therethrough;
said dilator projection portion being extended through the bore of the doughnut spring and into the radial leaf spring, with the application of compressive pressure to the outer surface of the proximal end causing the radial leaf spring to be distally advanced over the dilator projection portion which facilitates the opening of the aperture and the expansion of the reservoir, and the removal of the compressive pressure from the outer surface causing the radial leaf spring to be proximally withdrawn from over the dilator projection portion which facilitates the closing of the aperture and the collapse of the reservoir.

19. The injection site of claim 18 wherein said body comprises:
a generally cylindrical proximal portion defining said proximal end;
a generally cylindrical distal portion defining said distal end; and
a beveled shoulder formed between the proximal and distal portions;
the diameter of said distal portion exceeding the diameter of said proximal portion.

20. The injection site of claim 19 wherein the proximal portion of the body includes a centering ring formed thereon for maintaining the aperture in coaxial alignment with the fluid passage when the reseal member is moved between the first and second positions.

21. The injection site of claim 20 wherein the centering ring includes at least one notch disposed therein for venting the interior chamber during the movement of the reseal member from the first position to the second position.

22. The injection site of claim 19 wherein the distal portion of the body includes at least one compression ring formed thereon to assist in collapsing the reservoir when the reseal member moves from the second position to the first position.

23. The injection site of claim 19 wherein the distal portion of the body includes at least one set of arcuately contoured compression tabs formed thereon to assist in collapsing the reservoir when the reseal member moves from the second position to the first position.

24. The injection site of claim 19 wherein the distal portion of the body includes a plurality of elongate, longitudinally extending compression ribs formed thereon to assist in collapsing the reservoir when the reseal member moves from the second position to the first position.

25. The injection site of claim 18 wherein the doughnut spring includes a splined outer surface and the first end of the doughnut spring has a chamfered configuration.

26. The injection site of claim 25 wherein the doughnut spring is sized so as to be compressed between the distal end of the body and the housing when the reseal member is in the first position such that a pre-load is applied to the doughnut spring.

27. The injection site of claim 18 wherein the body includes an annular flange formed about and extending radially inward from the distal end thereof for forming a seal against the dilator projection portion.

28. The injection site of claim 18 wherein said body and said doughnut spring are each fabricated from silicone.

29. The injection site of claim 18 wherein the inner surface of the proximal end of the body has a generally semi-spherical configuration and the aperture extends axially between the outer surface of the proximal end and the apex of the inner surface thereof.

30. The injection site of claim 29 wherein the outer surface of the proximal end of the body includes a generally circular depression formed therein and the aperture extends axially between the approximate center of the depression of the apex of the inner surface.

31. The injection site of claim 18 wherein said radial leaf spring comprises a base portion and a plurality of flexible leaf portions which extend from the base portion and include slots therebetween, said leaf portions applying a radially inward biasing force to the proximal end of the body which normally closes the aperture, and said slots defining fluid-flow channels between the aperture and the reservoir when the reseal member is moved to the second position, and between the reservoir and the fluid passage during the return of the reseal member to the first position.

32. The injection site of claim 31 wherein each of the leaf portions includes an inner surface having a ramp formed thereon which extends to the base portion, said ramps contacting the dilator projection portion when the reseal member is distally advanced thereover which results in the outward flexion of the leaf portions and the opening of the aperture, the sizing of the ramps being adapted to prevent the bowing of the leaf portions when flexed outwardly by the dilator projection portion.

33. A needleless injection site, comprising:
 a housing defining a fluid passage having an internal diameter; and
 a reseal member disposed within the housing and including an openable and closable aperture and an expandable and collapsible reservoir which is adapted to retain a volume of fluid when expanded, the reseal member normally residing in a first position within the housing wherein the aperture is closed and the reservoir is collapsed;
 the reseal member being deformable such that the application of compressive pressure thereto will facilitate the movement thereof within the housing to a second position wherein the reservoir is expanded and the aperture is opened and placed into fluid communication with the fluid passage and the reservoir, and the removal of the compressive pressure therefrom will facilitate the resilient return thereof to the first position wherein the aperture is closed and the reservoir is collapsed, the reservoir having a volumetric capacity when expanded which is not less than the product of the internal diameter of the fluid passage and the distance of movement of the reseal member from the first position to the second position;
 the reseal member being cooperatively engaged to the housing such that the collapse of the reservoir which occurs when the reseal member resiliently returns to the first position forces any volume of fluid retained within the reservoir into the fluid passage for purposes of preventing the creation of a vacuum therewithin.

34. A needleless injection site, comprising:
 a housing defining a fluid passage; and
 a reseal member disposed within the housing and comprising:
  a resilient body having a distal end and a proximal end which defines inner and outer surfaces;
  an openable and closable aperture extending through the proximal end between the inner and outer surfaces thereof;
  a radial leaf spring disposed within the body and adapted to apply a radially inward biasing force to the proximal end which normally closes the aperture when no compressive pressure is applied to the outer surface of the proximal end; and
  an expandable and collapsible reservoir which is defined between the radial leaf spring and the body and is adapted to retain a volume of fluid when expanded, the reseal member normally residing in a first position within the housing wherein the aperture is closed and the reservoir is collapsed;
 the reseal member being deformable such that the application of compressive pressure thereto will facilitate the movement thereof within the housing to a second position wherein the reservoir is expanded and the aperture is opened and placed into fluid communication with the fluid passage and the reservoir, and the removal of the compressive pressure therefrom will facilitate the resilient return thereof to the first position wherein the aperture is closed and the reservoir is collapsed;
 the reseal member being cooperatively engaged to the housing such that the collapse of the reservoir which occurs when the reseal member resiliently returns to the first position forces any volume of fluid retained within the reservoir into the fluid passage for purposes of preventing the creation of a vacuum therewithin.

35. A needleless injection site, comprising:
 a housing having an inner surface which defines an interior chamber and a central opening which communicates with the interior chamber, an elongate, proximally extending dilator projection portion which defines a fluid passage, and at least one elongate slot which is formed within the inner surface and extends from the central opening to the interior chamber; and
 a reseal member disposed within the central opening and the interior chamber of the housing and including an openable and closable aperture and an expandable and collapsible reservoir which is adapted to retain a volume of fluid when expanded, the reseal member normally residing in a first position within the housing wherein the aperture is closed and the reservoir is collapsed;
 the reseal member being deformable such that the application of compressive pressure thereto will facilitate the movement thereof within the housing to a second position wherein the reservoir is expanded and the aperture is opened and placed into fluid communication with the fluid passage and the reservoir, and the removal of the compressive pressure therefrom will facilitate the resilient return thereof to the first position wherein the aperture is closed and the reservoir is collapsed, the slot being operable to vent the interior chamber during the movement of the reseal member from the first position to the second position;
 the reseal member being cooperatively engaged to the housing such that the collapse of the reservoir which occurs when the reseal member resiliently returns to the first position forces any volume of fluid retained within the reservoir into the fluid passage for purposes of preventing the creation of a vacuum therewithin.

\* \* \* \* \*

UNITED STATES PATENT AND TRADEMARK OFFICE
CERTIFICATE OF CORRECTION

PATENT NO. : 6,183,448 B1
DATED : February 6, 2001
INVENTOR(S) : Rod Ross and Gregory Hughes It is certified that error appears in the above-identified patent and that said Letters Patent is hereby corrected as shown below:

Column 5,
Lines 5-10, should recite: -- A method for assembling a head into a ring of a surgical device for cutting a cornea, wherein the head houses a blade, comprising: pushing a pair of tongues of a head into a pair of grooves of a ring in a direction that is essentially perpendicular to a longitudinal axis of the one of the grooves. --

Signed and Sealed this

Thirteenth Day of July, 2004

JON W. DUDAS
*Acting Director of the United States Patent and Trademark Office*